(12) United States Patent
Kim

(10) Patent No.: US 11,883,458 B2
(45) Date of Patent: Jan. 30, 2024

(54) HERB MEDICINE COMPOSITION FOR ALLEVIATING OR TREATING ASTHMA, AND ORIENTAL PHARMACOPUNCTURE SOLUTION CONTAINING SAME AND INJECTION CONTAINING SAME

(71) Applicant: Sung Ki Kim, Gunpo-si (KR)

(72) Inventor: Sung Ki Kim, Gunpo-si (KR)

( * ) Notice: Subject to any disclaimer, the term of this patent is extended or adjusted under 35 U.S.C. 154(b) by 164 days.

(21) Appl. No.: 17/607,164

(22) PCT Filed: Nov. 29, 2019

(86) PCT No.: PCT/KR2019/016793
§ 371 (c)(1),
(2) Date: Nov. 9, 2021

(87) PCT Pub. No.: WO2020/197036
PCT Pub. Date: Oct. 1, 2020

(65) Prior Publication Data
US 2022/0249589 A1     Aug. 11, 2022

(30) Foreign Application Priority Data

Mar. 22, 2019 (KR) .................. 10-2019-0033024

(51) Int. Cl.
| | | |
|---|---|---|
| *A61K 36/232* | (2006.01) | |
| *A61K 36/286* | (2006.01) | |
| *A61K 36/484* | (2006.01) | |
| *A61K 36/65* | (2006.01) | |
| *A61K 36/8905* | (2006.01) | |
| *A61K 36/9068* | (2006.01) | |
| *A61P 11/06* | (2006.01) | |
| *A61K 36/804* | (2006.01) | |
| *A61K 9/00* | (2006.01) | |

(52) U.S. Cl.
CPC .......... *A61K 36/804* (2013.01); *A61K 9/0019* (2013.01); *A61K 36/232* (2013.01); *A61K 36/286* (2013.01); *A61K 36/484* (2013.01); *A61K 36/65* (2013.01); *A61K 36/8905* (2013.01); *A61K 36/9068* (2013.01); *A61K 2300/00* (2013.01); *A61P 11/06* (2018.01)

(58) Field of Classification Search
None
See application file for complete search history.

(56) References Cited

FOREIGN PATENT DOCUMENTS

| KR | 10-2003-0007243 A | | 1/2003 |
|---|---|---|---|
| KR | 10-2009-0105314 A | | 10/2009 |
| KR | 1020090105314 A | * | 10/2009 |
| KR | 10-2013-0084043 A | | 7/2013 |
| KR | 1020130084043 A | * | 7/2013 |
| KR | 10-1367214 B1 | | 2/2014 |
| KR | 10-2017799 B1 | | 9/2019 |

OTHER PUBLICATIONS

Machinte translation, Description of KR1020090105314A (2023).*
Sung-Hwan Rhee, Soon-Shik Shin, and Yun-Ho Lee, Effects of Oyo-Tang Herbal Acupuncture on Immune Cells in Peripheral Blood and Serum IgE of Allergic Asthma in the Rats, The Journal of Korean Acupuncture & Moxibustion Medicine Society, Feb. 2001, pp. 29-39, vol. 18, No. 1.

* cited by examiner

*Primary Examiner* — H. Sarah Park
(74) *Attorney, Agent, or Firm* — KORUS Patent, LLC; Seong Il Jeong

(57) ABSTRACT

A composition for alleviating or treating asthma is proposed. A composition for alleviating or treating asthma contains, as an active ingredient, a concentrate obtained by distilling an extract obtained by extracting a herb medicine complex containing dried *Rehmanniae radix, Cyperus rotundus* L., *Paeonia lactiflora* Pall., *Zingiber officinale* Roscoe, *Angelica gigas* root, *Carthamus tinctorius* L., and *Glycyrrhiza uralensis* Fisch., using an extraction solvent, and can be provided in the form of an oriental pharmacopuncture solution or an injection.

5 Claims, No Drawings

HERB MEDICINE COMPOSITION FOR ALLEVIATING OR TREATING ASTHMA, AND ORIENTAL PHARMACOPUNCTURE SOLUTION CONTAINING SAME AND INJECTION CONTAINING SAME

TECHNICAL FIELD

The present disclosure relates to a herb medicine composition for alleviating or treating asthma using a complex herbal ingredient. More particularly, the present disclosure relates to a novel herb medicine composition that can be applied to acupuncture in oriental medicines by being used as an oriental pharmacopuncture solution or a direct injection unlike existing asthma medicines, thereby enabling asthma alleviation and/or breakthrough treatment.

BACKGROUND ART

Asthma is a chronic allergic respiratory disease caused by an allergic inflammatory reaction of the bronchi. It is also a condition in which the bronchi in the lungs are inflamed. In asthma, the bronchi often become narrowed, leading to symptoms including shortness of breath, wheezing, and severe coughing. These symptoms are recurrent and episodic. As the bronchial mucosa swells due to inflammation of the bronchi, which are the airways that carry air to the lungs, the bronchial muscles constrict. This causes narrowing of the bronchi, resulting in difficulty breathing.

Allergic diseases such as asthma are caused by a combination of genetic and environmental factors, and asthma is a representative intractable chronic disease that cannot be cured completely. Factors that cause asthma include causative agents and exacerbating factors. The causative agents are called allergens. Representative allergens include house dust mites, pollen, animal hair or dander, cockroaches, food, and drugs. Representative exacerbating factors include colds, tobacco smoke and indoor pollution, air pollution, food additives, physical activity such as exercise, climate change, yellow dust, and stress.

Asthma is a chronic inflammatory disorder of the airways, characterized by airway inflammation and airway hyperresponsiveness that lead to symptoms such as cough, wheezing, shortness of breath, and chest tightness. It also has a characteristic inflammatory pattern found in allergic diseases. When an allergen is detected, activated mucosal mast cells release bronchoconstriction mediators such as histamine (bronchospasm and inflammatory response), leukptrienes, and prostaglandin D2 (bronchoconstrictor). Increased numbers of activated eosinophils and invariant natural killer T cells (TCR of invariant natural killer T cells) release inflammatory substances, such as cytokines (regulating the overall inflammatory response) and chemokines (mobilizing inflammatory cells) that damage airway epithelial cells and contribute to symptoms. Along with the occurrence of hypertrophy and hyperplasia of smooth muscle cells, growth factors such as vascular endothelial growth factor (VEGF) induce proliferation of blood vessels in the airways and increase the thickness of the airway walls.

Asthma is a chronic and recurrent disease. Typical treatment methods include drug therapy that uses drugs to relieve symptoms and prevent recurrence, and avoidance therapy that finds causative agents of asthma, minimizes exposure to a causative allergen, and avoids exacerbating factors. Other treatment methods include immunotherapy that improves allergic constitution through injection of a small amount of a causative agent.

Asthma treatment drugs used in medicinal therapy can be divided into symptom relievers and disease controllers. Symptom relievers are used to relieve narrowed bronchi within a short period of time, whereas disease controllers are used to prevent asthma attacks by suppressing allergic inflammation of the bronchi. Representative symptom relievers include beta-2 agonists, xanthine drugs represented by theophylline, and parasympatholytic agents (anticholinergics), etc. Representative disease controllers include corticosteroids and leukotrienes.

However, the symptom relievers such as beta-2 agonists cannot fundamentally treat asthma, so they must be used regularly to be effective and thus may cause side effects in the human body. Long-term use of steroids can also cause serious side effects such as blood sugar rise, blood pressure rise, weight gain, mood changes, osteoporosis, gastric ulcer, etc. In addition, according to research, about 5% of all asthma patients developed drug resistance and did not respond to drugs at all, which could put them in a very dangerous state.

DISCLOSURE

Technical Problem

Accordingly, the present disclosure has been made keeping in mind the above problems occurring in the related art, and an objective of the present disclosure is to provide a herb medicine composition for alleviating or treating asthma using a natural herb medicine complex extract.

Another objective of the present disclosure is to provide an oriental pharmacopuncture solution containing the aforementioned herb medicine composition for alleviating or treating asthma, and an acupuncture method using the same.

Still another objective of the present disclosure is to provide an injection containing the aforementioned herb medicine composition for alleviating or treating asthma.

Technical Solution

In order to accomplish the above objectives, an aspect of the present disclosure provides a herb medicine composition for alleviating or treating asthma. The composition may include, as an active ingredient, a concentrate obtained by distilling an extract obtained by extracting a herb medicine complex comprising dried *Rehmanniae radix*, etc. using an extraction solvent.

Another aspect of the present disclosure provides a method of preparing a herb medicine composition for alleviating or treating asthma. The method may include: a first step of preparing a herb medicine complex; a second step of preparing a mixed solution by adding the herb medicine complex to an extraction solvent and stirring the resultant mixture; a third step of obtaining a concentrated extract by heating and distilling the mixed solution; and a fourth step of obtaining a concentrate by filtering the extract.

Advantageous Effects

Unlike existing asthma medicines that are delivered to the body through absorption into the bloodstream in the digestive system after oral administration, the herb medicine composition for alleviating or treating asthma according to the present disclosure can be used as an oriental pharmacopuncture solution or an injection, which is applied directly to asthma-inducing muscles or effective acupoints. Therefore, the present disclosure has an effect of enabling rapid asthma improvement without causing any toxicity, side effects, and drug resistance, and of enabling fundamental asthma improvement by repeatedly releasing the airway muscles to allow the airway muscles to stretch and contract normally.

In particular, the present disclosure has an excellent efficacy even in severe asthma patients who develop drug resistance and do not respond to drugs, accounting for about 5% of all asthma patients.

BEST MODE

In addition to the mechanisms known in the art in relation to the causes and treatment methods of bronchial asthma, the contraction of the intercostal muscles of the chest is very important as well as the contraction of the bronchial smooth muscles.

When a person breathes, the bronchial smooth muscles and the intercostal muscles of the chest stretch and contract repeatedly. When these muscles contract abnormally due to a certain physical reaction, this causes difficulty breathing. Depending on the degree of contraction, his or her body may enter into a very dangerous state.

One of the reasons for the contraction of the intercostal muscles and bronchial smooth muscles of the chest is cough caused by a cold. It is often said that "someone's ribs are broken or cracked while coughing". The reason why the ribs are broken and cracked and the bronchial smooth muscles and intercostal muscles contract abnormally during coughing is as follows. When a person coughs hard, air is forced to be instantly expelled into and out of the lungs as the muscles involved in breathing stretch and contract rapidly and instantly. At this time, severe pressure is exerted on the muscles, causing the muscles to contract abnormally.

The abnormally contracted breathing muscles contract and stiffen more and more as the years go by, and eventually, airflow is completely blocked, making breathing impossible.

Symptoms caused by such intercostal muscle contraction are as follows.

Heavy feeling in the chest
Tightness in the chest
Pressure in the chest
Shortness of breath getting worse when moving
People who suffer from difficulty breathing after a severe cough due to a cold even though there is no inflammation in the bronchi The present disclosure has been developed with reference to such a mechanism, and will be described in detail below.

A herb medicine composition for alleviating or treating asthma according to the present disclosure (hereinafter referred to as the "composition according to the present disclosure") may be prepared by performing a process including: a first step of preparing a herb medicine complex; a second step of preparing a mixed solution by adding the herb medicine complex to an extraction solvent and stirring the resultant mixture; a third step of obtaining a concentrated extract by heating and distilling the mixed solution; and a fourth step of obtaining a concentrate by filtering the extract.

First, the herb medicine complex in the first step will be described.

The herb medicine complex contains dried *Rehmanniae radix*, *Cyperus rotundus* L., *Paeonia lactiflora* Pall., *Zingiber officinale* Roscoe, *Angelica gigas* root, *Carthamus tinctorius* L., and *Glycyrrhiza uralensis* Fisch.

Of the ingredients contained in the herb medicine complex, dried *Rehmanniae radix* is the dried root of *Rehmannia glutinosa*. *Rehmannia glutinosa* is about 30 cm in height, with stems covered in dense short hairs. Its root is thick, is orange in color, and grows horizontally. Leaves growing from the roots are borne in clusters, and leaves borne on the stem are alternate. There are uneven sawtooths on the edge of the leaves, and veins on the back side of the leaves protrude while veins on the front side are dented concavely. The root of *Rehmannia glutinosa* is used in three types: fresh *Rehmanniae radix*, dug up from late autumn to before the following year's buds and buried in the sand in the shade; dried *Rehmanniae radix*, dug up before the soil freezes, stored in a hole in the ground, and dried in the shade; and prepared *Rehmanniae radix*, steamed and dried.

Fresh *Rehmanniae radix* is used as a blood nourishing agent. Dried *Rehmanniae radix* has a slightly bitter taste and is used to treat depression. Prepared *Rehmanniae radix* is used as a blood enriching agent and a tonic. All these are known to be very effective when the body is weak, especially when the body is weakened by tuberculosis. *Rehmannia glutinosa* is a plant propagated mainly by rhizomes and growing well in sunny, warm, well-drained, fertile soil.

*Cyperus rotundus* L. is a perennial plant belonging to the family Cyperaceae, and grows in sandy soils of fields, roadsides, and riversides. The whole plant is aromatic, and elongated rhizomes grow horizontally, with widely spaced tubers. The tubers have white flesh and are aromatic. The tubers of *Cyperus rotundus* L. are used in oriental medicine. The tubers are ovoid or fusiform in shape, with pointed ends, about 1 to 3.5 cm in length, about 1cm in diameter, and sometimes have very short rhizomes at the ends. The tubers are dark brown externally, often have brown, tough hairs, are hard, and are reddish-yellow and shiny in cross-section. The tubers are collected in spring and autumn, dried, and then roasted to remove hairs. *Cyperus rotundus* L. mainly acts on the liver meridian and the triple energizer meridian, but also acts on the lung meridian and the gallbladder meridian. *Cyperus rotundus* L. is flat and slightly cold in nature, is non-toxic, and is spicy, slightly bitter, and sweet in taste. *Cyperus rotundus* L. is effective in relieving stress by facilitating the flow of vital energy and in regulating menstruation to relieve pain. In particular, it is known to be effective for pain, especially menstrual pain, and menstrual irregularity, which are caused by stagnation of vital energy.

*Paeonia lactiflora* Pall. is a plant cultivated as an ornamental or medicinal herb. Roots are used as an analgesic, antipyretic, and diuretic. Main ingredients include peonoside, paeoniflorin, β-sitosterol, paeonine, gallotanin, benzoic acid, astragalin, etc.

*Zingiber officinale* Roscoe is a plant believed to have originated in southeastern Asia. Its rhizome is aromatic and tangy in taste, so it is used as a spice of food, a medicinal herb, etc. The leaf-like rhizome grows to about 1 m in height. Leaves develop from leaf sheaths surrounding the rhizome, and two elongated leaves with a length of 15 to 30 cm are alternate in vertical rows. Flowers are about 2.5 cm in thickness and about 4 to 7.6 cm in length, with overlapping green bracts with yellow edges. Each bract surrounds 1 small yellow-green/purple flower. *Zingiber officinale* Roscoe contains about 2% of essential oil. Its main ingredient is zingiberene, and zingerone has a tingling taste. The essential oil is extracted and used to make food and perfume. As a spice, *Zingiber officinale* Roscoe has a slightly bitter taste and is usually dried and ground for use in bread, confectionery, curry dishes, sauces, pickles, and *Zingiber officinale* Roscoe ale, etc. The fresh rhizome, green *Zingiber officinale* Roscoe, is used in cooking. Peeled rhizomes are boiled and pickled in syrup, and in some regions, including Japan, they are sliced and eaten during meals to cleanse the palate.

*Zingiber officinale* Roscoe is also used as a medicinal herb to treat tympanites and abdominal pain.

*Angelica gigas* root is the root of *Angelica gigas* Nakai. *Angelica gigas* Nakai grows wild in mountains, but is mainly cultivated. Its stem is about 1 to 2 m in height, and its root is used as a medicinal herb. The root is thick, contains essential oils, and has a strong aroma. The root is about 20 to 25 cm in length and about 1 to 5 cm in diameter. Main ingredients are essential oils, uterine excitatory ingredients, sucrose, and vitamin E. *Angelica gigas* root is mild in nature, is non-toxic, and is sour, sweet, and slightly bitter in taste. It acts mainly on the three meridians of the heart, liver, and spleen. It is effective for menstrual pain, and is used in combination with *Paeonia obovata, Corydalis tuber, Cyperus rotundus* L., etc. It is also effective for amenorrhea and menstrual irregularity. For symptoms such as palpitations, forgetfulness, insomnia, and mental instability caused by blood deficiency of the heart, *Angelica gigas* root is used to enrich the blood and relax the mind. For symptoms such as weight loss and a haggard face caused by blood deficiency of the spleen, *Angelica gigas* root is used to nourish the blood and strengthen the spleen. For symptoms such as dizziness, eye strain, tinnitus, and muscle spasms, *Angelica gigas* root is used to nourish the blood and the liver. In addition, for symptoms such as trauma such as bruises and sprains and for those such as internal bleeding, blood stasis, swelling, and pain caused by vascular disease, *Angelica gigas* root is used to promote blood circulation and relieve pain.

*Carthamus tinctorius* L. is a plant belong to the family Asteraceae. It is a biennial herb native to Egypt and is hairless. Leaves are alternate and broad lanceolate in shape. Flowers bloom in July to August, are thistle-like in shape, and are reddish-yellow in color. Each flower is borne at the end of a main stem and at the end of a branch. The flowers are used as a red dye and used for food dyeing, and in oriental medicine, are used as a medicinal herb for gynecological diseases and pain relief. Young shoots are eaten, and seeds are used to make oil. *Carthamus tinctorius* L. is known to be effective in promoting blood circulation, promoting the energy flow of meridians, removing blood stasis, and relieving pain.

*Glycyrrhiza uralensis* Fisch. is used as a medicinal herb by drying roots, and was given its name due to its sweet taste. *Glycyrrhiza uralensis* Fisch. contains glycyrrhizin, glabric acid, sucrose, glucose, liquiritin, and lycorisidine. Glycyrrhizin has the effect of detoxifying diphtheria toxin, tetanus toxin, codeine hydrochloride, strychnine acetate, snake venom, pufferfish venom, etc. It also has an anti-inflammatory effect for suppressing edema. A study has revealed that glycyrrhizin lowers blood pressure by lowering the cholesterol level in the blood, promotes the secretion of bile, and has antitussive and analgesic effects. A study for the digestive system has revealed that *Glycyrrhiza uralensis* Fisch. has an ulcer-suppressing action as a result of administrating its decoction to ulcer-induced dogs. Other studies have revealed that *Glycyrrhiza uralensis* Fisch. has a significant inhibitory effect on experimentally induced bladder stones, and has a significant inhibitory effect on ascites cancer and liver cancer in an anticancer activity test. *Glycyrrhiza uralensis* Fisch. is one of the most used medicinal herbs in oriental medicine.

The herb medicine complex in the first step used for preparing the composition according to the present disclosure contains 90 to 130 parts by weight of *Cyperus rotundus* L., 80 to 110 parts by weight of *Paeonia lactiflora* Pall., 80 to 110 parts by weight of *Zingiber officinale* Roscoe, 50 to 120 parts by weight of *Angelica gigas* root, 50 to 85 parts by weight of *Carthamus tinctorius* L., and 40 to parts by weight of *Glycyrrhiza uralensis* Fisch. with respect to 100 parts by weight of dried *Rehmanniae radix*, preferably 95 to 120 parts by weight of *Cyperus rotundus* L., 85 to 110 parts by weight of *Paeonia lactiflora* Pall., 90 to 110 parts by weight of *Zingiber officinale* Roscoe, 75 to 110 parts by weight of *Angelica gigas* root, 65 to 85 parts by weight of *Carthamus tinctorius* L., and 50 to 80 parts by weight of *Glycyrrhiza uralensis* Fisch. with respect to 100 parts by weight of dried *Rehmanniae radix*, and more preferably 95 to 110 parts by weight of *Cyperus rotundus* L., 90 to 105 parts by weight of *Paeonia lactiflora* Pall., 95 to 105 parts by weight of *Zingiber officinale* Roscoe, 85 to 110 parts by weight of *Angelica gigas* root, 70 to 80 parts by weight of *Carthamus tinctorius* L., and 60 to 80 parts by weight of *Glycyrrhiza uralensis* Fisch. with respect to 100 parts by weight of dried *Rehmanniae radix*.

Next, the second step is a process of preparing the mixed solution by adding the herb medicine complex of the first step to the extraction solvent and sufficiently stirring the resultant mixture under 25° C. to 30° C. At this time, it is preferable to use 3.0 to 4.0 L of the extraction solvent per 1 kg of the herb medicine complex, more preferably 3.1 to 3.3 L of the extraction solvent per 1 kg of the herb medicine complex, and more preferably 3.15 to 3.25 L of the extraction solvent per 1 kg of the herb medicine complex. When the amount of extraction solvent is less than 3.0 L, this small amount of extraction solvent evaporates too quickly during distillation in the third step, which may make it difficult to extract an active ingredient. On the other hand, when the amount thereof exceeds 4 L, the distillation time is prolonged, which may make the process uneconomical.

In addition, as the extraction solvent, it is preferable in terms of extracting the proper active ingredient from the herb medicine complex to use a mixed solvent in which water and an aqueous alcohol solution are mixed, preferably a mixed solvent in which water and an aqueous ethanol solution having a concentration of 50% to 70% by volume are mixed in a volume ratio of 1:0.2 to 0.5, and more preferably a mixed solvent in which water and an aqueous ethanol solution having a concentration of 60% to 65% by volume are mixed in a volume ratio of 1:0.20 to 0.35.

Next, the third step is a process of obtaining the concentrated extract by heating the mixed solution of the herb medicine complex and the extraction solvent to extract the active ingredient from the herb medicine complex, and distilling the solvent. The heating and distilling are preferably performed so that the volume of the mixed solution satisfies Equation 1 below.

$15\% \leq \{(\text{volume of mixed solution before heating} - \text{volume of extract after heating})/\text{volume of mixed solution before heating} * 100\%\} \leq 20\%$, preferably $16.5\% \leq \{(\text{volume of mixed solution before heating} - \text{volume of extract after heating})/\text{volume of mixed solution before heating} * 100\%\} \leq 20.0\%$ [Equation 1]

At this time, the heating temperature is 75° C. to 90° C., preferably 80° C. to 85° C. When the heating temperature exceeds 90° C., the ethanol component evaporates too quickly, so that a sufficient amount of active ingredient may not be extracted. On the other hand, when the heating temperature is less than 75° C., the active ingredient may be difficult to extract, and the process of preparing the extract through distillation may be prolonged.

Next, the fourth step is a process of obtaining the concentrate (or extract) from the concentrated extract by filtering the extract concentrated in the third step using a general method.

The composition according to the present disclosure prepared in such a manner may be provided in the form of an oriental pharmacopuncture solution or an injection that is administered directly through the skin rather than orally, thereby alleviating and/or treating asthma more rapidly and effectively than conventional oral asthma treatment medicines.

In addition, the oriental pharmacopuncture solution and/or the injection may further contain a lubricant, an emulsifier, a suspending agent, a preservative, etc. which are harmless to the human body.

In addition, in a preferred example of acupuncture using the composition according to the present disclosure, acupuncture may be performed using the composition as an oriental pharmacopuncture solution in such a manner that the solution is filled into an oriental pharmacopuncture solution injection device, after which the solution is injected at the acupuncture point Ren 22, called "Cheon Dol" in Korean, which is effective for asthma.

MODE FOR INVENTION

Hereinafter, examples of the present disclosure will be described in more detail.

EXAMPLE

Example 1: Preparation of Herb Medicine Composition for Alleviating or Treating Asthma (1) Preparation of Herb Medicine Complex A herb medicine complex was prepared by mixing 100 parts by weight of dried *Rehmanniae radix,* 100 parts by weight of *Cyperus rotundus* L., 100 parts by weight of *Paeonia lactiflora* Pall., 100 parts by weight of *Zingiber officinale* Roscoe, 100 parts by weight of *Angelica gigas* root, 75 parts by weight of *Carthamus tinctorius* L., and 75 parts by weight of *Glycyrrhiza uralensis* Fisch.

(2) Preparation of Concentrate

Distilled water and an aqueous ethanol solution having a concentration of 62.5% were mixed in a volume ratio of 1:0.25 to prepare mixed solvent.

Then, 3.25 L of the mixed solvent added per 1 kg of the herb medicine complex to prepare a mixed solution.

Then, the mixed solution was stirred and heated to 80° C. to 82° C. for distillation. The mixed solution was heated and distilled until the volume of the mixed solution satisfies Equation 1-1 below, to obtain a concentrated extract.

Finally, the concentrated extract was filtered to prepare a herb medicine composition for alleviating or treating asthma in the form of a concentrate.

$$17.5\% \leq \{(\text{volume of mixed solution before heating} - \text{volume of extract after heating})/\text{volume of mixed solution before heating} * 100\%\} \leq 18.0\% \quad \text{[Equation 1-1]}$$

Examples 2 to 3 and Comparative Examples 1 to 2

Herb medicine compositions for alleviating or treating asthma according to Examples 2 to 3 and Comparative Examples 1 to 2 were prepared in the same manner as in Example 1, except that each herb medicine complex having a composition ratio as illustrated in Table 1 below was prepared, after which each herb medicine composition was prepared using the same.

TABLE 1

| Classification (parts by weight) | Dried Rehmanniae radix | Cyperus rotundus L. | Paeonia lactiflora Pall. | Zingiber officinale Roscoe | Angelica gigas root | Carthamus tinctorius L. | Glycyrrhiza uralensis Fisch. |
|---|---|---|---|---|---|---|---|
| Example 1 | 100 | 100 | 100 | 100 | 100 | 75 | 75 |
| Example 2 | 100 | 95 | 95 | 107 | 100 | 80 | 70 |
| Example 3 | 100 | 105 | 100 | 95 | 85 | 70 | 80 |
| Comparative Example 1 | 100 | 70 | 100 | 100 | 70 | 75 | 75 |
| Comparative Example 2 | 100 | 100 | 70 | 100 | 100 | 40 | 75 |

Preparation Example 1: Preparation of Injection

The herb medicine composition prepared in Example was mixed with sterile physiological saline (N/S) (Lot No.: 12062, supplier: JW Pharmaceutical), after which the mixture was diluted to a concentration of 35% by volume to prepare an injection.

Preparation Examples 2 to 3 and Comparative Preparation Examples 1 to 2: Preparation of Injection Injections according to Preparation Examples 2 to 3 and Comparative Preparation Examples 1 to 2 were prepared in the same manner as in Preparation Example 1, except that each injection was prepared using each of the herb medicine compositions of Examples 2 to 3 and Comparative Preparation Examples 1 to 2 in lieu of that of Example 1.

Experimental Example 1: Measurement of White Blood Cell, Eosinophil, and Differential Cell Count Ovalbumin was administered to BALB/c mice to induce asthma. The total white blood cell (WBC) count, eosinophil count, and differential cell count (IgE) in bronchoalveolar lavage fluid (BALF) were measured.

As experimental animals, BALB/c mice (supplier: Samtako Korea), which have been widely used in asthma tests, were used. Female BALB/c mice were used and were 6 weeks old at the time of acquisition and 7 weeks old at the time of the experiment. After acquisition, the mice were acclimatized in an animal test room for 6 days, and observed at least once a day. During the acclimatization period, the mice were distinguished by skin mark using a red oil magic pen. During the administration and observation period, the mice were distinguished by skin mark using a black oil magic pen. An individual identification card was attached to a breeding cage. The mice were housed in a breeding area under the condition of a temperature of 23±3° C., a relative humidity of 55±15%, a ventilation frequency of 10 to 20 times/hr, an illumination time of 12 hours, and an illuminance of 150 to 300 Lux. During the period of acclimatization and administration, at least four mice were housed in each polycarbonate breeding cage containing an appropriate amount of rug. During the acclimatization period, mice determined to be healthy were weighed and ranked according to weight. The mice were distributed into groups so that the mean weights of each group were equal.

As an asthma inducer, refrigerated ovalbumin (OVA) (catalog No.: A5503, supplier: Sigma Aldrich, Louis, Missouri, USA) was used. As an adjuvant, refrigerated aluminum hydroxide (Alum) (catalog No.: 77161, supplier: Thermo Fisher Scientific Inc, Waltham, Massachussets, USA) was used. As a positive control material, dexamethasone (DEX) stored at room temperature (product No.: 13099, supplier: SAMNAM Pharm, Chungcheongnam-do, Korea) was used.

For asthma induction, the mice were injected with an intraperitoneal injection of OVA 20 μg+, Alum 1 mg+, and sterile physiological saline 500 μL/head twice a week for 2 weeks.

The asthma-induced mice were injected with physiological saline as a negative control, dexamethasone as a positive control, and Preparation Example 1 and the others twice a week for 4 weeks as illustrated in Table 2 below. The injection volume is as illustrated in Table 2 below.

TABLE 2

| Classification | Types of herb medicine composition | Number of asthma-induced mice (gender) | Injection volume (μL/g) | | |
|---|---|---|---|---|---|
| | | | Physiological saline | DEX | Herb medicine composition |
| Negative control | — | 3 (Female) | 30 | — | — |
| Positive control | — | 3 (Female) | — | 28 | 0 |
| Preparation Example 1 | Example 1 | 3 (Female) | — | — | 30 |
| Preparation Example 2 | Example 2 | 3 (Female) | — | — | 30 |
| Preparation Example 3 | Example 3 | 3 (Female) | — | — | 30 |
| Comparative Preparation Example 1 | Comparative Example 1 | 3 (Female) | — | — | 30 |
| Comparative Preparation Example 2 | Comparative Example 2 | 3 (Female) | — | — | 30 |

After 4 weeks, the measurement of the white blood cell (WBC) count, eosinophil count, and IgE was performed using mouse blood. The mean values thereof were calculated, and the results are illustrated in Table 3 below.

TABLE 3

| Classification | WBC count ($\times 10^3$ cells/μl) | Eosinophil count ($\times 10^2$ cells/μl) | IgE (μg/ml) |
|---|---|---|---|
| Negative control | 61.20 | 2.32 | 59.53 |
| Positive control | 39.83 | 1.41 | 23.45 |
| Preparation Example 1 | 40.51 | 1.63 | 29.77 |
| Preparation Example 2 | 41.65 | 1.69 | 32.50 |
| Preparation Example 3 | 43.89 | 1.85 | 32.06 |
| Comparative Preparation Example 1 | 52.71 | 1.97 | 48.04 |
| Comparative Preparation Example 2 | 51.86 | 2.12 | 45.41 |

Referring to Table 3, the results revealed that in the case of the positive control and Preparation Examples to 3, the WBC count, eosinophil count, and IgE were significantly low compared to the negative control. In addition, in the case of Preparation Examples 1 to 3, the WBC count, eosinophil count, and IgE were slightly high compared to the positive control, but significantly low compared to the negative control. This indicated that the present disclosure was suitable as a herb medicine composition for alleviating or treating asthma. On the other hand, in the case of Comparative Preparation Examples 1 to 2, the WBC count, eosinophil count, and IgE were low compared to the negative control, but still high compared to the positive control and Preparation Examples 1 to 3.

Experimental Example 2: Measurement of Asthma Alleviation Effect Through Pharmacopuncture Treatment As an oriental pharmacopuncture solution, the W herb medicine composition prepared in Example 1 was prepared without dilution.

Then, acupuncture was performed on 10 asthma patients using the pharmacopuncture solution. The acupuncture was performed by injecting the pharmacopuncture solution at the acupuncture point Ren 22, called "Cheon Dol" in Korean.

The acupuncture was performed twice a week for 12 weeks, and whether the patients's asthma was alleviated was checked every 4 weeks. The results are illustrated in Table 4 below.

TABLE 4

| Classification | Week 4 | Week 8 | Week 12 |
|---|---|---|---|
| Very alleviated | 2 | 3 | 6 |
| Alleviated | 3 | 5 | 4 |
| Slightly alleviated | 4 | 2 | 0 |
| No change | 1 | 0 | 0 |

The results of the above experiment revealed that asthma could be greatly alleviated through acupuncture with injection using the oriental pharmacopuncture solution according to the present disclosure, and the alleviation of asthma was possible even with short-term treatment, which in turn would be expected to enable fundamental treatment of asthma rather than temporary symptom alleviation with long-term treatment.

Although several embodiments of the present disclosure have been described for illustrative purposes, the scope of the disclosure is not limited thereto. It will be appreciated by those skilled in the art that various modifications may be made without departing from the scope of the disclosure.

The invention claimed is:

1. A herb medicine composition for alleviating or treating asthma, the composition comprising, as an active ingredient, a concentrate obtained by distilling an extract obtained by extracting a herb medicine complex comprising dried *Rehmanniae radix, Cyperus rotundus* L, *Paeonia lactiflora* Pall, *Zingiber officinale* Roscoe, *Angelica gigas* root, *Carthamus tinctorius* L, and *Glycyrrhiza uralensis* Fisch, using an extraction solvent, wherein the herb medicine complex comprises 90 to 130 parts by weight of the *Cyperus rotundus* L, 80 to 110 parts by weight of the *Paeonia lactiflora* Pall, 80 to 110 parts by weight of the *Zingiber officinale* Roscoe, 50 to 1.20 parts by weight of the *Angelica gigas* root, 30 to 85 parts by weight of the *Carthamus tinctorius* L, and 40 to 80 parts by weight of the *Glycyrrhiza uralensis* Fisch with respect to 100 parts by weight of the dried *Rehmanniae radix*.

2. The composition of claim 1, wherein the extract comprises 3.00 to 4.00 L of the extraction solvent per 1 kg of the herb medicine complex.

3. The composition of claim 1, wherein the extraction solvent comprises water and an aqueous ethanol solution having a concentration of 50% to 70% b volume in a volume ratio of 1:0.2 to 0.5.

4. An oriental pharmacopuncture solution containing a herb medicine composition that comprises, as an active ingredient, a concentrate obtained by distilling an extract obtained by extracting a herb medicine complex comprising dried *Rehmanniae radix, Cyperus rotundus* L, *Paeonia lactiflora* Pall, *Zingiber officinale* Roscoe, *Angelica gigas* root, *Carthamus tinctorius* L, and *Glycyrrhiza uralensis* Fisch, using an extraction solvent, wherein the herb medicine complex comprises 90 to 130 parts by weight of the *Cyperus rotundus* L, 80 to 110 parts by weight of the *Paeonia lactiflora* Pall, 80 to 110 parts by weight of the *Zingiber officinale* Roscoe, 50 to 120 parts by weight of the *Angelica gigas* root, 30 to 85 parts by weight of the *Carthamus tinctorius* L, and 40 to 80 parts by weight of the *Glycyrrhiza uralensis* Fisch with respect to 100 parts by weight of the dried *Rehmanniae radix*.

5. The oriental pharmacopuncture solution of claim 4, wherein acupuncture is performed by injecting the oriental pharmacopuncture solution at the acupuncture point Ren 22, called "Cheon Dol" in Korean.

* * * * *